(12) United States Patent
Possemiers et al.

(10) Patent No.: US 9,550,213 B2
(45) Date of Patent: Jan. 24, 2017

(54) PROCESS FOR CLASSIFYING WATER-ABSORBING POLYMER BEADS

(71) Applicant: BASF SE, Ludwigshafen (DE)

(72) Inventors: Karl J. Possemiers, Speyer (DE); Thomas Pfeiffer, Boehl-Iggelheim (DE); Matthias Weismantel, Jossgrund (DE); Rüdiger Funk, Niedernhausen (DE); Monte Peterson, Pearland, TX (US); Sven Serneels, Township of Washington, NJ (US); Jeffrey Johnson, Lake Jackson, TX (US); Ronny De Kaey, Mortsel (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/779,990

(22) PCT Filed: Mar. 18, 2014

(86) PCT No.: PCT/EP2014/055365
§ 371 (c)(1),
(2) Date: Sep. 25, 2015

(87) PCT Pub. No.: WO2014/154522
PCT Pub. Date: Oct. 2, 2014

(65) Prior Publication Data
US 2016/0030979 A1  Feb. 4, 2016

Related U.S. Application Data

(60) Provisional application No. 61/805,938, filed on Mar. 28, 2013.

(51) Int. Cl.
| | | |
|---|---|---|
| *B07B 1/00* | (2006.01) |
| *B07B 1/46* | (2006.01) |
| *B07B 9/00* | (2006.01) |
| *C08J 3/24* | (2006.01) |
| *C08L 33/02* | (2006.01) |
| *A61L 15/60* | (2006.01) |
| *C08F 220/06* | (2006.01) |
| *C08J 3/12* | (2006.01) |
| *G01N 15/02* | (2006.01) |

(52) U.S. Cl.
CPC .......... *B07B 1/46* (2013.01); *A61L 15/60* (2013.01); *B07B 9/00* (2013.01); *C08F 220/06* (2013.01); *C08J 3/12* (2013.01); *C08J 3/245* (2013.01); *C08L 33/02* (2013.01); *G01N 15/0272* (2013.01); *B07B 2201/04* (2013.01); *C08J 2333/02* (2013.01)

(58) Field of Classification Search
CPC ....................................... B07B 1/46; B07B 9/00
USPC ........................................................ 209/233
See application file for complete search history.

(56) References Cited

U.S. PATENT DOCUMENTS

| 7,967,148 B2 * | 6/2011 | Stueven | .................... B07B 1/46 209/11 |
| 8,443,982 B2 * | 5/2013 | Stueven | .................... B07B 1/46 209/21 |
| 8,844,729 B2 * | 9/2014 | Stueven | .................... B07B 1/46 209/11 |
| 9,089,624 B2 * | 7/2015 | Whitmore | ............... A61F 13/15 |
| 2004/0242761 A1 | 12/2004 | Dairoku et al. | |
| 2009/0261023 A1 | 10/2009 | Stueven et al. | |
| 2009/0266747 A1 | 10/2009 | Stueven et al. | |
| 2012/0211699 A1 * | 8/2012 | Daniel | ................... B01J 20/264 252/194 |

FOREIGN PATENT DOCUMENTS

| WO | WO-2008/037672 A1 | 4/2008 | |
| WO | WO-2008/037675 A1 | 4/2008 | |
| WO | WO 2008037672 A1 * | 4/2008 | ............... B07B 1/00 |
| WO | WO 2008037675 A1 * | 4/2008 | ............... B07B 1/46 |

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.

International Search Report in International Patent Application No. PCT/EP2014/055365, dated Jun. 12, 2014.

* cited by examiner

*Primary Examiner* — Terrell Matthews

(74) *Attorney, Agent, or Firm* — Marshall, Gerstein & Borun LLP

(57) ABSTRACT

A process for classifying water-absorbing polymer particles, wherein screens having different mesh sizes are used before and after surface postcrosslinking to remove the undersize (fines).

14 Claims, No Drawings

PROCESS FOR CLASSIFYING WATER-ABSORBING POLYMER BEADS

CROSS-REFERENCE TO RELATED APPLICATIONS

This is the U.S. National Stage of PCT/EP2014/055365, filed Mar. 18, 2014, which claims the benefit of U.S. Provisional Patent Application No. 61/805,938, filed Mar. 28, 2013, incorporated herein by reference in its entirety.

The present invention relates to a process for classifying water-absorbing polymer particles, wherein screens having different mesh sizes are used before and after surface postcrosslinking to remove the undersize (fines).

The production of water-absorbing polymers is described in the monograph "Modern Superabsorbent Polymer Technology", F. L. Buchholz and A. T. Graham, Wiley-VCH, 1998, pages 71 to 103.

As products which absorb aqueous solutions, water-absorbing polymers are used for the production of diapers, tampons, sanitary napkins and other hygiene articles, but also as water-retaining agents in market gardening.

The properties of the water-absorbing polymers can be adjusted via the degree of crosslinking. With increasing degree of crosslinking, the gel strength rises and the centrifuge retention capacity (CRC) falls.

To improve the use properties, for example saline flow conductivity (SFC) in the diaper and absorbency under load (AUL), water-absorbing polymer particles are generally surface postcrosslinked. This increases only the degree of crosslinking of the particle surface, which allows absorbency under load (AUL) and centrifuge retention capacity (CRC) to be at least partly decoupled. This surface postcrosslinking can be performed in the aqueous gel phase. However, dried, ground and screened-off polymer particles (base polymer) are preferably coated on the surface with a surface postcrosslinker, dried and thermally surface postcrosslinked. Crosslinkers suitable for this purpose are compounds which comprise at least two groups which can form covalent bonds with the carboxylate groups of the polymer particles.

The water-absorbing polymer particles are used in the hygiene sector. Here, for example, particle sizes between 150 and 850 μm are used and the polymer particles are classified to these particle sizes actually in the course of the production process. In this case, continuous screening machines with two screens are used, wherein the screens used having the mesh sizes of 150 and 850 μm. Particles having a particle size of up to 150 μm fall through both screens and are collected as undersize (fines) at the bottom of the screening machine. Particles having a particle size of greater than 850 μm remain on the uppermost screen as oversize and are discharged. The product fraction having a particle size of greater than 150 to 850 μm is removed as midsize between the two screens of the screening machine. Depending on the screening quality, each particle size fraction still comprises a proportion of particles with the wrong particle size as erroneous discharge. For example, the midsize fraction may also comprise a proportion of particles having a particle size of 150 μm or less.

Discharged undersize and oversize is typically recycled into the production. The undersize can be added, for example, to the polymerization. The oversize is typically comminuted, which inevitably also leads to the occurrence of further undersize.

In the conventional classifying operations, different problems occur when particular polymer particles are classified. The most frequent problem is the blockage of the screen surface and the deterioration in the classifying efficiency and the classifying ability. A further problem is the caking tendency of the product particles which leads to undesired agglomerates before, after and during the screening. The process step of screening therefore cannot be performed such that it is free of disruptions, often accompanied by unwanted shutdowns in production. Such disruptions are found to be particularly problematic in the continuous production process. The overall result is, however, insufficient separation efficiency in the screening.

A higher screening quality is typically achieved by adding substances to the product which serve to increase the free flow and/or the mechanical stability of the polymer particles. In general, a free-flowing product is achieved when assistants, for example surfactants, which prevent mutual adhesion of the individual particles, are added to the polymer particles, usually after the drying and/or in the course of the surface postcrosslinking. In other cases, attempts are made to influence the caking tendencies by process technology measures.

In order to achieve higher separation efficiencies without further product additives, improvements by virtue of alternative screening units have been proposed. For instance, higher separation efficiencies are achieved when screen orifice areas are driven in spiral form. This is, for example, the case in tumbling screen machines. When, however, the throughput of such screening apparatus is increased, the above problems are enhanced, and it becomes ever more impossible to maintain the high classifying capability.

The addition of screening aids such as screening balls, PVC friction rings, Teflon-friction rings or rubber cubes on the screen surface only helps insignificantly to improve the separation efficiency. Particularly in the case of amorphous polymer material, such as water-absorbing polymer particles, this can cause increased attrition.

A general overview of classification can be found, for example, in Ullmanns Encyklopädie der technischen Chemie, 4th edition, volume 2, pages 43 to 56, Verlag Chemie, Weinheim, 1972.

It is an object of the present invention to provide an improved classifying process for the production of water-absorbing polymer particles.

This object is achieved by a process for preparing water-absorbing polymer particles, comprising
i) classification of the water-absorbing polymer particles, the undersize being removed by means of a screen having the mesh size $m_1$,
ii) surface postcrosslinking of the classified polymer particles,
iii) classification of the surface postcrosslinked polymer particles, the undersize being removed by means of a screen having the mesh size $m_2$, and
iv) recycling the undersize from step i) and iii),
wherein the throughput per hour of water-absorbing polymer particles in the course of classification in step i) is at least 100 kg/h per $m^2$ of screen area and the mesh size $m_1$ in step i) is greater than the mesh size $m_2$ in step iii).

The classification process according to the invention is particularly advantageously performed continuously. The throughput of water-absorbing polymer particles in step i) is preferably at least 200 kg/$m^2$h, more preferably at least 300 kg/$m^2$h, most preferably at least 400 kg/$m^2$ h.

Undersize (fines) refers here to a sieve cut which has a lower mean particle size in comparison to the target product.

The invention is based on the finding that recycling of surface postcrosslinked undersize had a negative impact on the product quality. By using a larger mesh size than necessary for the undersize separation prior to the surface postcrosslinking, the ratio non-surface postcrosslinked undersize to surface postcrosslinked undersize can be positively changed.

The screening result may, especially at high throughputs, be improved further when the midsize (product fraction) is removed by means of at least two screens of different mesh sizes.

The screening result may, especially at high throughputs, be improved further when the oversize is removed by means of at least two screens of different mesh sizes.

In the process according to the invention, the screen fractions can be combined in different ways to give particle size fractions, for example in the sequence (2,1), (3,1), (2,1,1), (1,2,1), (2,2,1), (3,1,1), (1,3,1), (3,2,1), (2,3,1) or (3,3,1), where the number of figures in one set of brackets represents the number of particle size fractions, the particle size fractions are arranged from left to right in the brackets in product flow sequence, and the numerical values themselves represent the number of successive screen fractions which are combined to give the particular particle size fraction.

The number of particle size fractions is preferably at least 3. The number of screens used is preferably at least (n+1).

In a preferred embodiment of the present invention, at least two screen fractions obtained in succession in product flow direction are combined to give one particle size fraction, and the mesh sizes of the screens on which these screen fractions are obtained differ preferably by in each case typically at least 50 µm, preferably by in each case at least 100 µm, preferably by in each case at least 150 µm, more preferably by in each case at least 200 µm, most preferably by in each case at least 250 µm.

In a further preferred embodiment of the present invention, the at least two screen fractions obtained first in product flow direction are combined to give one particle size fraction, and the mesh sizes of the screens on which these screen fractions are obtained differ preferably by in each case at least 500 µm, preferably by in each case at least 1000 µm, more preferably by in each case at least 1500 µm, most preferably by in each case at least 2000 µm.

The mesh size $m_1$ in step i) is preferably at least 180 µm, more preferably at least 200 µm, most preferably at least 250 µm. The mesh size $m_2$ $m_1$ in step iii) is preferably not more than 150 µm, more preferably not more than 120 µm, most preferably not more than 100 µm. The mesh size $m_1$ in step i) is preferably at least 20 µm, more preferably at least 30 µm, most preferably at least 50 µm, greater than the mesh size $m_2$ in step iii).

During the classification, the water-absorbing polymer particles preferably have a temperature of from 40 to 120° C., more preferably from 45 to 100° C., most preferably from 50 to 80° C.

In a preferred embodiment of the present invention, classification is effected under reduced pressure. The pressure is preferably 100 mbar less than ambient pressure.

The water-absorbing polymer particles are preferably flowed over with a gas stream, more preferably air, during the classification. The gas rate is typically from 0.1 to 10 m³/h per m² of screen area, preferably from 0.5 to 5 m³/h per m² of screen area, more preferably from 1 to 3 m³/h per m² of screen area, the gas volume being measured under standard conditions (25° C. and 1 bar). The gas stream is more preferably heated before entry into the screen apparatus, preferably to a temperature of from 40 to 120° C., more preferably to a temperature of from 60 to 100° C., most preferably to a temperature of from 70 to 80° C. The water content of the gas stream is preferably less than 5 g/kg, more preferably less than 3.5 g/kg, most preferably less than 3 g/kg. A gas stream with low water content can be obtained, for example, by condensing an appropriate amount of water out of a gas stream with relatively high water content by cooling.

In a preferred embodiment of the present invention, a plurality of screening machines is operating in parallel.

In a more embodiment of the present invention, tumbling screen machines are partly or wholly thermally insulated.

In a most embodiment of the present invention, the screens have guide devices that deflect the water-absorbing polymer particles in the direction of the middle of the screen or in a spiral path toward the exit orifice of the screen. Advantageously, the screens have guide devices of both types. The exit orifice of the screen is at the screen edge. The polymer beads which do not pass through the mesh of the screen are withdrawn via the exit orifice.

The screening machines are typically electrically grounded.

The screening apparatus suitable for the classification process according to the invention are subject to no restriction; preference is given to planar screening processes; very particular preference is given to tumbling screen machines. The screening apparatus is typically agitated to support the classification. This is preferably done in such a way that the material to be classified is conducted in spiral form over the screen. This forced vibration has an amplitude of preferably from 0.7 to 40 mm, more preferably from 1.2 to 30 mm, most preferably from 1.5 to 25 mm, and a frequency of preferably from 1 to 100 Hz, more preferably from 2.5 to 25 Hz, most preferably from 5 to 10 Hz.

The production of the water-absorbing polymer particles is described in detail hereinafter:

The water-absorbing polymer particles to be used in the process according to the invention may be produced by polymerizing monomer solutions comprising at least one ethylenically unsaturated monomer a) bearing acid groups, at least one crosslinker b), at least one initiator c), optionally one or more ethylenically unsaturated monomer d) copolymerizable with the ethylenically unsaturated monomer a), optionally one or more water-soluble polymer e) and water.

The water-absorbing polymer particles are produced by polymerizing a monomer solution or suspension, and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight and most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

Further suitable examples are iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraaminehexaacetic acid, N,N-bis(2-hydroxyethyl)glycine and trans- 1,2-diaminocyclohexanetetraacetic acid, and salts thereof. The amount used is typically 1 to 30 000 ppm based on the monomers a), preferably 10 to 1000 ppm, preferentially 20 to 600 ppm, more preferably 50 to 400 ppm, most preferably 100 to 300 ppm.

The monomer solution or suspension is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is preferably carried out at the monomer stage. This is typically accomplished by mixing in the neutralizing agent as an aqueous solution or preferably also as a solid. The degree of neutralization is preferably from 50 to 90 mol %, more preferably from 60 to 85 mol % and most preferably from 65 to 80 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The resulting polymer gel is dried. The driers are not subject to any restriction. However, the drying of the polymer gel is preferably performed with a belt drier until the residual moisture content is preferably 0.5 to 10% by weight, more preferably 1 to 7% by weight and most preferably 2 to 5% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Subsequently, the dried polymer gel is ground and classified. The apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

Polymer particles with too small a particle size lower the saline flow conductivity (SFC). The proportion of undersize particles (fines) should therefore be low.

Undersize particles are therefore removed and recycled into the process. This is preferably done before, during or immediately after the polymerization, i.e. before the drying of the polymer gel. The undersize particles can be moistened with water and/or aqueous surfactant before or during the recycling.

It is also possible to remove undersize particles in later process steps, for example after the postcrosslinking or another coating step. In this case, the undersize particles recycled are postcrosslinked or coated in another way, for example with fumed silica.

When a kneading reactor is used for polymerization, the undersize particles are preferably added during the last third of the polymerization.

When the undersize particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

When the undersize particles are added at a very late stage, for example not until an apparatus connected downstream of the polymerization reactor, for example an extruder, the undersize particles can be incorporated into the resulting polymer gel only with difficulty. Insufficiently incorporated, undersize particles are, however, detached again from the dried polymer gel during the grinding, are therefore removed again in the course of classification and increase the amount of undersize particles to be recycled.

Polymer particles of oversize particle size lower the free swell rate. The proportion of oversize particles should therefore likewise be small.

Oversize particles are therefore typically removed and recycled into the grinding of the dried polymer gel.

To improve the properties, the polymer particles are subsequently be thermally surface postcrosslinked. Suitable surface postcrosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1,DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and derivatives thereof in WO 2003/031482 A1.

The amount of surface postcrosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal surface postcrosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface postcrosslinking temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

Subsequently, the surface postcrosslinked polymer particles are classified again, excessively small and/or excessively large polymer particles being removed and recycled into the process.

The water-absorbing polymer particles produced by the process according to the invention have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Fluid Retention Capacity in Saline, After Centrifugation".

The water-absorbing polymer particles produced by the process according to the invention have an absorption under a pressure of 49.2 g/cm$^2$ of typically at least 15 g/g, preferably at least 20 g/g, more preferably at least 22 g/g, especially preferably at least 24 g/g and most preferably at least 26 g/g. The absorption under a pressure of 49.2 g/cm² of the water-absorbing polymer particles is typically less than 35 g/g. The absorption under a pressure of 49.2 g/cm² is determined analogously to EDANA recommended test method No. WSP 242.2-05 "Absorption under Pressure, Gravimetric Determination", except that a pressure of 49.2 g/cm² is established instead of a pressure of 21.0 g/cm².

Methods:

The analyses should, unless stated otherwise, be performed at an ambient temperature of 23±2° C. and a relative air humidity of 50±10%. The water-absorbing polymer particles are mixed thoroughly before the analysis.

Centrifuge Retention Capacity

The centrifuge retention capacity (CRC) is determined by the EDANA recommended test method No. WSP 241.2-05 "Centrifuge Retention Capacity".

Absorption Under a Pressure of 49.2 g/cm²

The absorption under a pressure of 49.2 g/cm² (AUL0.7 psi) is determined analogously to the EDANA recommended test method No. WSP 242.2-05 "Absorption under Pressure", except that a pressure of 49.2 g/cm² (AUL0.7 psi) is established instead of a pressure of 21.0 g/cm² (AUL0.3 psi).

Particle Size Distribution

The particle size distribution of the water-absorbent polymer particles is determined with the Camziser® image analysis sytem (Retsch Technology GmbH; Haan; Germany).

For determination of the average particle diameter and the particle diameter distribution the proportions of the particle fractions by volume are plotted in cumulated form and the average particle diameter is determined graphically.

The average particle diameter (APD) here is the value of the mesh size which gives rise to a cumulative 50% by weight.

EXAMPLES

Example 1a

Base Polymer A and SXL Polymer A 4813 g sodium acrylate (37.3 wt.-% aqueous solution), 458 g acrylic acid, 202 g deionized water and 8.38 g polyethylene glycol (400) diacrylate were mixed and gassed with nitrogen for displacement of oxygen. The neutralization degree of this mixture corresponded to 75 mol % and the solid content was 41% by weight. The polymerization was performed in a double arm kneter (LUK 8.0K2; Coperion Werner & Pfleiderer GmbH & Co. KG; Stuttgart, Germany) after initiation by addition of 8.94 g sodium peroxodisulfate (15 wt.-% aqueous solution), 0.72 g hydrogen peroxide (2.5 wt.-% aqueous solution) and 8.81 g ascorbic acid (0.5 wt.-% aqueous solution). 6 minutes after initiation, the temperature of the polymer mixture reached 86° C. ($T_{max}$) and was removed as polymer gel from the reactor 30 minutes after initiation with a temperature of 63° C.

The resulting polymer gel was divided into 3 parts of each 1500 g.

1500 g polymer gel (Base Polymer A Gel) was dried at 150° C. for 90 minutes in a forced-air drying cabinet and a loading of the drying sieves with 0.519 g/cm², afterwards comminuted with a roll mill (gap width: 5 mm, 1000 µm, 600 µm and 400 µm) and then classified by sieving to a particle size range of 150 µm to 850 µm.

The resulting polymer particles (Base Polymer A) thus obtained had a centrifuge retention capacity (CRC) of 31.0 g/g.

The surface of 20 g of this base polymer (Base Polymer A) was contacted in a mixing unit (Waring® Blender) with a solution of 0.03 g of N-(2-hydroxyethyl)-2-oxazolidinone, 0.03 g of 1,3-propanediol, 0.23 g isopropanol and 0.31 g of water then heated to 185° C. for 60 minutes, and screened off to from 150 to 850 µm (SXL Polymer A). The amount of separated undersize fraction (SXL Polymer Fines A) was 0.60 g (3.0%).

The surface postcrosslinked water-absorbing polymer particles (SXL Polymer A) used had the following profile of properties:

CRC: 26.8 g/g
AUL0.7 psi: 24.6 g/g

Example 1b

Base Polymer A Fines and SXL Polymer A Fines

Base Polymer Fines A were generated by repeating example 1 a, however the dried polymer was comminuted with an ultracentrifugal mill (ZM 200; Retsch) and the resulting particles were classified by sieving to a particle size range of 90 to 150 µm. These Base Polymer Fines had an average particle diameter (APD) of 124 µm.

SXL Polymer Fines were generated by repeating the surface crosslinking step of example 1a, however the particles comminuted with the ultracentrifugal mill and sieved to a particle size of less than 425 µm were used. After the heating step at 185° C. the particles were classified by sieving to a particle size range of 90 to 150 µm. These SXL Polymer Fines A had an average particle diameter (APD) of 126 µm.

Example 2

Base Polymer B-1 and SXL Polymer B-1

1500 g polymer gel (Base Polymer A Gel), as described in example 1 a, was powdered uniformly on the surface nearly at the same time as used in example 1a (without gel storage) by means of a 250 µm screen and a spoon with 153.8 g undersize particles (Base Polymer Fines A) and then mixed with a meat chopper. This polymer gel was dried, comminuted as described in example 1a and then sieved by means of 850µm-sieve to particles with a particle size less than 850 µm. These particles were divided with a sample divider.

152.8 g of the divided particles were classified by sieving to a particle size range of 150 to 850 µm (Base Polymer B-1). The sieves had a diameter of 200 mm each and the screening was performed for ten seconds (1740 kg/m²h).

The resulting polymer particles (Base Polymer B-1) thus obtained had a centrifuge retention capacity (CRC) of 31.0 g/g. The amount of undersize fraction (Base Polymer Fines B-1) was 8.3 g (5.5%).

The surface of 20 g of this base polymer (Base Polymer B-1) was contacted in a mixing unit (Waring® Blender) with a solution of 0.03 g of N-(2-hydroxyethyl)-2-oxazolidinone, 0.03 g of 1,3-propanediol, 0.23 g isopropanol and 0.31 g of water then heated to 185° C. for 60 minutes, and screened off to from 150 to 850 µm (SXL Polymer B-1). The amount of separated undersize fraction (SXL Polymer Fines B-1) was 0.92 g (4.6%).

The resulting water-absorbing polymer particles (SXL Polymer B-1) were analyzed. The results are compiled in Table 1.

Example 3

Base Polymer B-2 and SXL Polymer B-2

152.5 g of the divided particles, resulting from 1500 g polymer gel (Base Polymer A Gel) which was powdered uniformly with 153.8 g undersize particles, described in example 2, were classified by sieving to a particle size range of 200 to 850 μm (Base Polymer B-2). The sieves had a diameter of 200 mm each and the screening was performed for ten seconds (1740 kg/m$^2$h).

The resulting polymer particles (Base Polymer B-2) thus obtained had a centrifuge retention capacity (CRC) of 30.6 g/g. The amount of undersize fraction (Base Polymer Fines B-2) was 15.4 g (10.1%).

The surface of 20 g of this base polymer (Base Polymer B-2) was contacted in a mixing unit (Waring® Blender) with a solution of 0.03 g of N-(2-hydroxyethyl)-2-oxazolidinone, 0.03 g of 1,3-propanediol, 0.23 g isopropanol and 0.31 g of water then heated to 185° C. for 60 minutes, and screened off to from 150 to 850 μm (SXL Polymer B-2). The amount of separated undersize fraction (SXL Polymer Fines B-2) was 0.40 g (2.0%).

The resulting water-absorbing polymer particles (SXL Polymer B-2) were analyzed. The results are compiled in Table 1.

Example 4

Base Polymer C-1 and SXL Polymer C-1

1500 g polymer gel (Base Polymer A Gel), as described in example 1 a, was powdered uniformly on the surface nearly at the same time as used in example 1a (without gel storage) by means of a 250 μm screen and a spoon with 153.8 g undersize particles (SXL Polymer Fines A) and then mixed with a meat chopper. This polymer gel was dried, comminuted as described in example 1a and then sieved by means of 850 μm-sieve to particles with a particle size less than 850 μm. These particles were divided with a sample divider.

151.2 g of the divided particles were classified by sieving to a particle size range of 150 μm to 850 μm (Base Polymer C-1). The sieves had a diameter of 200 mm each and the screening was performed for ten seconds (1740 kg/m$^2$h).

The resulting polymer particles (Base Polymer C-1) thus obtained had a centrifuge retention capacity (CRC) of 28.3 g/g. The amount of undersize fraction (Base Polymer Fines C-1) was 8.5 g (5.6%).

The surface of 20 g of this base polymer (Base Polymer C-1) was contacted in a mixing unit (Waring® Blender) with a solution of 0.03 g of N-(2-hydroxyethyl)-2-oxazolidinone, 0.03 g of 1,3-propanediol, 0.23 g isopropanol and 0.31 g of water then heated to 185° C. for 60 minutes, and screened off to from 150 to 850 μm (SXL Polymer C-1). The amount of separated undersize fraction (SXL Polymer Fines C-1) was 0.96 g (4.8%).

The resulting water-absorbing polymer particles (SXL Polymer B-1) were analyzed. The results are compiled in Table 1.

Example 5

Base Polymer C-2 and SXL Polymer C-2

152.5 g of the divided particles, resulting from 1500 g polymer gel (Base Polymer A Gel) which was powdered uniformly with 153.8 g undersize particles, described in example 4, were classified by sieving to a particle size range of 200 to 850 μm (Base Polymer C-2). The sieves had a diameter of 200 mm each and the screening was performed for ten seconds (1740 kg/m$^2$h).

The resulting polymer particles (Base Polymer C-2) thus obtained had a centrifuge retention capacity (CRC) of 28.1 g/g. The amount of undersize fraction (Base Polymer Fines C-2) was 15.0 g (9.9%).

The surface of 20 g of this base polymer (Base Polymer B-2) was contacted in a mixing unit (Waring® Blender) with a solution of 0.03 g of N-(2-hydroxyethyl)-2-oxazolidinone, 0.03 g of 1,3-propanediol, 0.23 g isopropanol and 0.31 g of water then heated to 185° C. for 60 minutes, and screened off to from 150 to 850 μm (SXL Polymer C-2). The amount of separated undersize fraction (SXL Polymer Fines C-2) was 0.44 g (2.2%).

The resulting water-absorbing polymer particles (SXL Polymer C-2) were analyzed. The results are compiled in Table 1.

TABLE 1

Properties of the water-absorbing polymer particles

| Ex. | Water-absorbing Polymer Particles | CRC [g/g] | AUL0.7 psi [g/g] |
|---|---|---|---|
| 2*) | SXL Polymer B-1 | 25.7 | 22.5 |
| 3 | SXL Polymer B-2 | 26.2 | 23.3 |
| 4*) | SXL Polymer C-1 | 21.1 | 21.4 |
| 5 | SXL Polymer C-2 | 22.0 | 21.7 |

*)comparative example

The results show that recycling of surface postcrosslinked undersize had a negative impact on the centrifuge retention capacity (CRC). There is a CRC reduction of 4.6 g/g (comparison of examples 2 and 4) and 4.2 g/g (comparison of examples 3 and 5). The results show also that recycling of surface postcrosslinked undersize had a negative impact on the absorption under a pressure of 49.2 g/cm$^2$ (AUL0.7 psi). There is a AUL0.7psi reduction of 1.1 g/g (comparison of examples 2 and 4) and 0.3 g/g (comparison of examples 3 and 5). By using a larger mesh size than necessary for the undersize separation prior to the surface posrcrosslinking, the amount of surface postcrosslinked undersize can be significantly reduced. That means also the negative impact of recycled surface postcrosslinked undersize can be significantly reduced.

The negative impact of recycled surface postcrosslinked undersize cannot be compensated by using a reduced amount of crosslinker b). Reducing the amount of crosslinker b) results in a increased CRC but also results in a reduced AUL0.7 psi.

The results show further that using a larger mesh size than necessary for the undersize separation prior to the surface posrcrosslinking had a small positive impact on the centrifuge retention capacity (CRC). There is a CRC raise of 0.5 g/g (comparison of examples 2 and 3) and 0.9 g/g (comparison of examples 4 and 5).

The invention claimed is:

1. A process for preparing water-absorbing polymer particles, comprising
   i) classifying the water-absorbing polymer particles, undersize being removed using a screen having the mesh size $m_1$,
   ii) surface postcrosslinking the classified polymer particles,
   iii) classifying the surface postcrosslinked polymer particles, undersize being removed using a screen having the mesh size $m_2$, and
   iv) recycling the undersize from step i) and iii), wherein a throughput per hour of the water-absorbing polymer particles in the course of classification in step i) is at least 100 kg/h per $m^2$ of screen area and the mesh size $m_1$ in step i) is greater than the mesh size $m_2$ in step iii).

2. The process according to claim 1, wherein a product fraction is removed in step i) and/or step iii) using at least two screens of different mesh sizes.

3. The process according to claim 1, wherein oversize is removed in step i) and/or step iii) using at least two screens of different mesh sizes.

4. The process according to claim 1, wherein the mesh size $m_1$ in step i) is at least 180 μm.

5. The process according to claim 1, wherein the mesh size $m_2$ in step iii) is not more than 150 μm.

6. The process according to claim 1, wherein the mesh size $m_1$ in step i) is at least 30 μm greater than the mesh size $m_2$ in step iii).

7. The process according to claim 1, wherein the water-absorbing polymer particles, during the classification in step i) and/or step iii), have a temperature of from 40 to 120° C.

8. The process according to claim 1, wherein classification in step i) and/or step iii) is effected under reduced pressure.

9. The process according to claim 1, wherein the water-absorbing polymer particles are flowed over by a gas stream during the classification in step i) and/or step iii).

10. The process according to claim 9, wherein the gas stream has a temperature of from 40 to 120° C.

11. The process according to claim 9, wherein the gas stream has a steam content of less than 5 g/kg.

12. The process according to claim 1, wherein the water-absorbing polymer particles have been obtained by polymerizing an aqueous monomer solution.

13. The process according to claim 1, wherein the water-absorbing polymer particles comprise at least 50 mol % of at least partly neutralized polymerized acrylic acid.

14. The process according to claim 1, wherein the water-absorbing polymer particles, before step ii), have a centrifuge retention capacity of at least 15 g/g.

* * * * *